April 9, 1946. B. R. LEACH Plant Pat. 675
AZALEA PLANT
Filed June 6, 1945
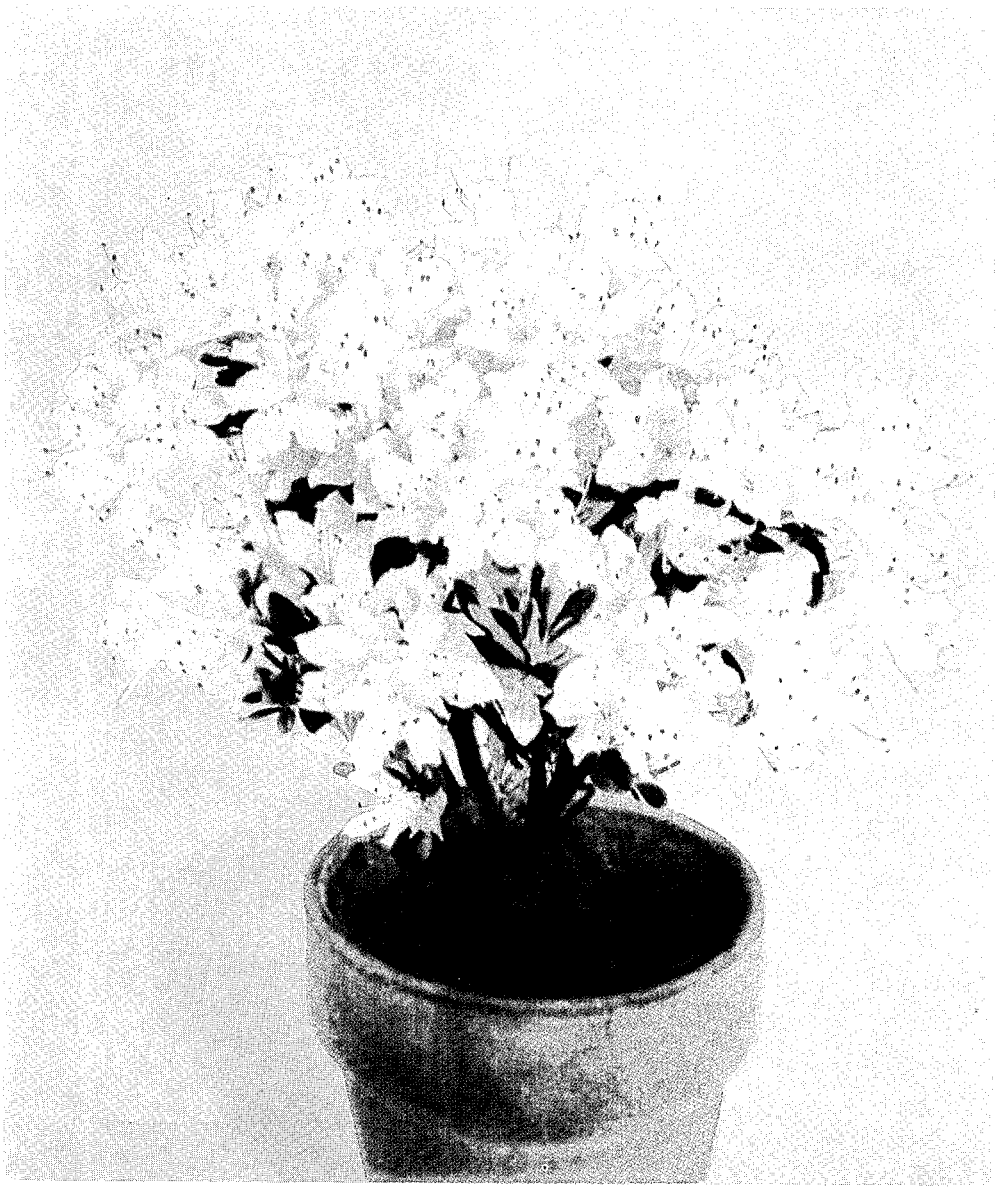
INVENTOR
Benjamin R. Leach
By Orville M. Kile
Plant Pat. Agt.

Patented Apr. 9, 1946

Plant Pat. 675

UNITED STATES PATENT OFFICE

675

AZALEA PLANT

Benjamin R. Leach, Cinnaminson, N. J.

Application June 6, 1945, Serial No. 597,736

1 Claim. (Cl. 47—60)

My new discovery consists of an improvement in the Kurume type of azaleas which are used much for greenhouse forcing. It is an excellent grower and can be forced more easily than any other Kurume variety known to me. In fact it can be easily forced for Christmas even though bed grown and potted as late as October 1st. Since my new variety is exceptionally hardy it is also very adaptable to outdoor growing.

This new variety appeared in my gardens several years ago as a seedling of unknown parentage, being one of many different types produced from a quantity of seed. Since that time I have improved it by budding and selection and developed considerable stocks in which the characteristics have proved to be permanently fixed.

The accompanying illustration shows, in approximately its true colors, a three-year-old forced plant of my new variety which annually has been heavily trimmed for cuttings.

A detailed description of the plant and flower follows. References to color plates indicate Ridgway's Color Standards and Nomenclature.

*The plant*

Growth: This variety is twice as rapid a grower as such standard varieties as Hinodigeri or Snow, adding 10 to 12 inches per year. It can easily be grown on its own roots without grafting.

Form: Upright, heavy and compact, forming rounded symmetrical bushes.

Blooming habit: Plant is a complete mass of bloom which lasts 2 to 3 weeks. Flowers are borne usually in groups of three on short stems. Can easily be forced to bloom by Christmas.

Hardiness: Completely wood hardy as far north as New York city. Exceptionally bud hardy, in fact more hardy than any other Kurume azalea known to me.

Stems: Woody; slender; straight; much branched.

Foliage:

*Quantity.*—Moderate.

*Size.*—Small, not exceeding ¾ inch in length at the time plant is in bloom.

*Type.*—Evergreen, making a decorative plant even when not in bloom.

*Shape.*—Narrow; elliptical.

*Color.*—New growth Parrot Green (Plate VI). Old growth between Cress Green and Dark Cress Green (Plate XXXI) on upper side, Rainette Green (Plate XXXI) on under side.

*Flowers*

Size: Large for Kurume type azalea, averaging 2 inches in diameter if petals are spread. However the usual form of the flower remains tubular and the average of the spread in that form is 1¼ inches. Length of the tube is 1 to 1¼ inches.

Form: Tubular, with five deep-cut lobes or petals. Edges of most petals are slightly wavy and turn in such a way as to form a slight point at the tip, particularly of the three upper petals.

Color: The color is new and distinct in Kurume azaleas and is difficult to describe. The nearest found in Ridgway's is Eosine Pink (Plate I) although when first open the flowers have a slight apricot tinge also. As the flowers become older they become somewhat lighter in color.

Texture: Petals have considerable substance although delicate in appearance.

Persistence: Flowers last many days and cling when dead.

Reproductive organs:

*Pistil.*—One long pistil approximately 1½ inches long arises from the ovary, through the center of the tubular flower, extending beyond the corolla and stamens. The *style* is pink tinged and the *stigma* is Tyrian Rose (Plate XII).

*Stamens.*—Five stamens are attached to the corolla at its base and arise from the center of the flower surrounding the pistil. *Filaments* are of unequal lengths but all slightly shorter than the pistil, and their color is slightly darger than the petals. *Anthers* are large and dark red.

*Comparisons*

The variety which is most like my new azalea variety is the Kurume variety Hinodigeri, particularly with respect to shape of flower, but the important differences between the two varieties are as follows:

1. Their flowers are of entirely different colors.
2. The flower of my new variety is larger.
3. The plant of my new variety is much heavier and more upright in growth.
4. My variety grows much more rapidly.
5. My variety is very hardy, which is not true of Hinodigeri.
6. My variety can be more easily forced for early blooming.

Having thus disclosed my variety, I claim:

The new and useful variety of azalea plant substantially as shown and described, characterized particularly by its heavy upright growth; its hardiness; the ease with which it can be forced for early blooming; its rapid growth; ease of propagation without grafting; and its abundant production of large flowers of distinct apricot-pink color.

BENJAMIN R. LEACH.